(12) United States Patent
Johannesson et al.

(10) Patent No.: US 7,270,079 B2
(45) Date of Patent: *Sep. 18, 2007

(54) MILK CONVEYER DEVICE

(75) Inventors: Leif Börje Johannesson, Tullinge (SE); Ola Sandberg, Gnesta (SE); Lars Andersson, Sodertalje (SE)

(73) Assignee: Lattec I/S, Hillerod (DK)

( * ) Notice: Subject to any disclaimer, the term of this patent is extended or adjusted under 35 U.S.C. 154(b) by 0 days.

This patent is subject to a terminal disclaimer.

(21) Appl. No.: 11/325,517

(22) Filed: Jan. 5, 2006

(65) Prior Publication Data

US 2006/0107899 A1    May 25, 2006

Related U.S. Application Data

(62) Division of application No. 10/739,310, filed on Dec. 19, 2003, now Pat. No. 7,162,971.

(60) Provisional application No. 60/434,415, filed on Dec. 19, 2002.

(51) Int. Cl.
*A01J 5/013* (2006.01)
*A01J 7/02* (2006.01)

(52) U.S. Cl. .................. 119/14.18; 119/14.02; 119/14.01

(58) Field of Classification Search ......... 119/14.01, 119/14.02, 14.18
See application file for complete search history.

(56) References Cited

U.S. PATENT DOCUMENTS 3,186,434 A    6/1965    Hrdina (Continued)

FOREIGN PATENT DOCUMENTS

AU    A.-70 458/81    8/1982

(Continued)

OTHER PUBLICATIONS

English Abstract of Australian Patent Application No. AU 9470269 A, Mar. 2, 1995.

(Continued)

*Primary Examiner*—Michael J. Corona
*Assistant Examiner*—Bret Hayes
(74) *Attorney, Agent, or Firm*—Roberts, Mlotkowski & Hobbes P.C.

(57) ABSTRACT

The invention relates to a milk conveyer device (100) for an animal. The milk conveyer device is to be implemented in a milking arrangement which comprises a milk storage reservoir (101) coupled to a milking attachment for attaching to an animal to be milked through a main milk conduit (103, 105). A sample element (109, 111) extracts milk, which is collected in a sample reservoir (115, 117). The sample reservoir (115,117) is connected to an analysis element (129) through an analysis conduit (123, 125). During the flow of the milk from the sample reservoir to the analysis element (129), the milk itself provides a cleaning effect. The flow is initially at a high flow rate and later at a reduced flow rate. A plurality of analysis conduits (123, 125) are connected to the analysis element (129), which comprises a selector unit (127), which couples milk from one of the analysis conduits (123, 125) to the analysis element (129). The device provides a self-cleaning effect and a low carry-over of milk between two successive milking operations, i.e. between the milk of two different animals.

16 Claims, 10 Drawing Sheets

U.S. PATENT DOCUMENTS

| | | | |
|---|---|---|---|
| 3,868,970 A | 3/1975 | Ayers et al. | |
| 3,995,495 A | 12/1976 | Aegidius | |
| 4,207,922 A | 6/1980 | Andrieux et al. | |
| 4,366,839 A | 1/1983 | Slavin | |
| 4,462,425 A | 7/1984 | Mehus | |
| RE31,659 E | 9/1984 | Brown | |
| 4,476,808 A | 10/1984 | Meermoller et al. | |
| 4,569,236 A | 2/1986 | Kitchen et al. | |
| 4,572,105 A | 2/1986 | Chowdhury et al. | |
| 4,702,197 A | 10/1987 | Icking et al. | |
| 4,771,007 A | 9/1988 | Tippetts et al. | |
| 4,793,285 A * | 12/1988 | Marshall | 119/14.02 |
| 4,911,891 A | 3/1990 | Platt | |
| 5,388,549 A | 2/1995 | Holroyd | |
| 5,743,209 A | 4/1998 | Bazin et al. | |
| 5,762,020 A | 6/1998 | van der Lely | |
| 5,901,748 A | 5/1999 | Jessop | |
| 6,089,242 A | 7/2000 | Buck | |
| 6,814,025 B2 | 11/2004 | Chen et al. | |
| 2005/0223996 A1 | 10/2005 | Bosma et al. | |

FOREIGN PATENT DOCUMENTS

| | | |
|---|---|---|
| AU | A 70 458/81 | 8/1982 |
| DE | 1 773 656 | 8/1972 |
| DE | 2 354 820 | 11/1974 |
| DE | 35 02 858 A1 | 10/1985 |
| DE | 3502858 A1 | 10/1985 |
| DE | 43 43 717 A1 | 6/1995 |
| DE | 195 47 892 A1 | 7/1997 |
| EP | 0 98 966 A2 | 6/1983 |
| EP | 0 098 966 | 1/1984 |
| EP | 0 161 552 B1 | 7/1990 |
| EP | 0 564 023 B1 | 6/1993 |
| EP | 0 564 023 | 10/1993 |
| EP | 0 713 641 | 5/1996 |
| EP | 0 713 641 A1 | 5/1996 |
| EP | 0 749 681 B1 | 12/1996 |
| EP | 749681 B1 | 12/1996 |
| FR | 22 50 111 | 7/1975 |
| FR | 2250111 | 7/1975 |
| FR | 2 645 705 | 10/1990 |
| GB | 2 107 282 A | 4/1983 |
| GB | 2107282 A | 4/1983 |
| GB | 2 231 658 A | 11/1990 |
| GB | 2231658 | 11/1990 |
| GB | 2 285 037 A | 6/1995 |
| GB | 2 285 037 A | 6/1995 |
| SE | 515 093 | 6/2001 |
| WO | 92/15196 | 9/1992 |
| WO | WO 92/15196 | 9/1992 |
| WO | 03/090522 | 11/2003 |
| WO | WO 03/090522 | 11/2003 |

OTHER PUBLICATIONS

Patent Abstracts of Japan of Japanese Patent Publication No. 08136420 A, published Mar. 31, 1996, Shinichi.

English Abstract of French Patent Publication No. FR 2250111 A, Jul. 4, 1975.

Full English Translation of German Laid Open Specification 1 773, 656, published Aug. 10, 1972.

Translation of the abstract for French Patent No. 2 645 705, published Oct. 19, 1990.

Translation of the abstract for Swedish Patent No. 515 093, published Jun. 11, 2001.

Translation of the Abstract for European Patent No. 0 098 966, published Jan. 25, 1984.

English Abstract of Australian Patent Application No. AU 9470269 A, Mar. 2, 1995.

Patent Abstract of Japan of Japanese Patent Publication No. 08136420 A, published May 31, 1996, Shinichi.

English Abstract of French Patent Publication No. FR 2250111 A, Jul. 4, 1975.

U.S. Appl. No. 11/623,029, filed Jan. 12, 2007, inventor L. B. Johannesson et al.

* cited by examiner

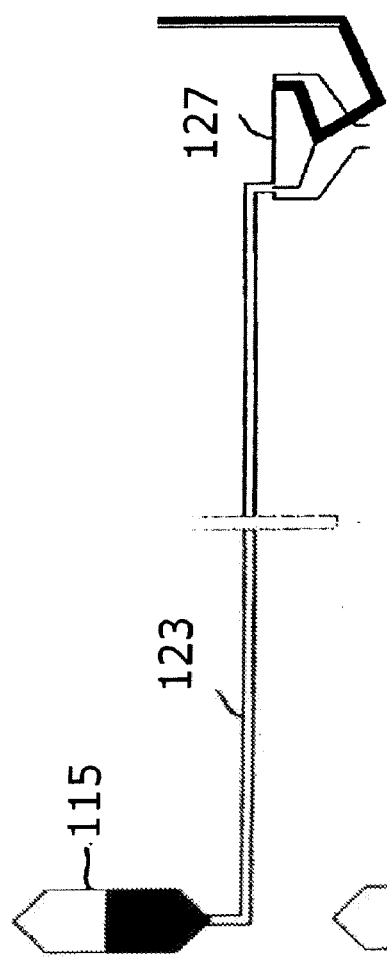
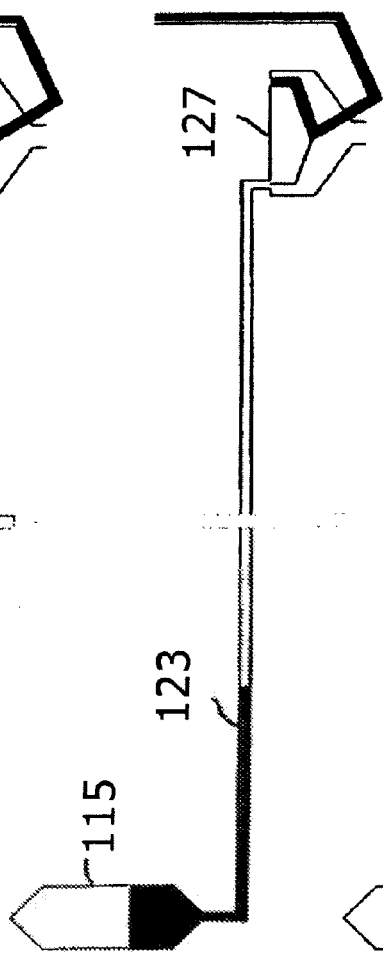
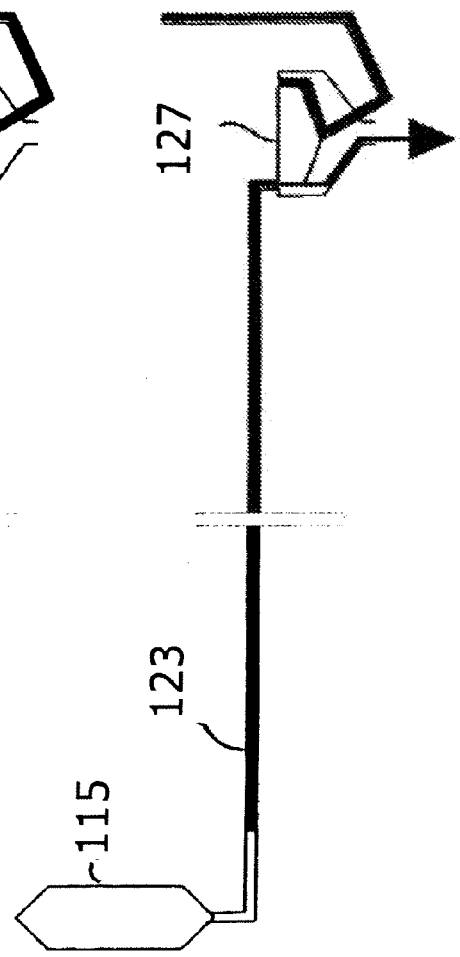

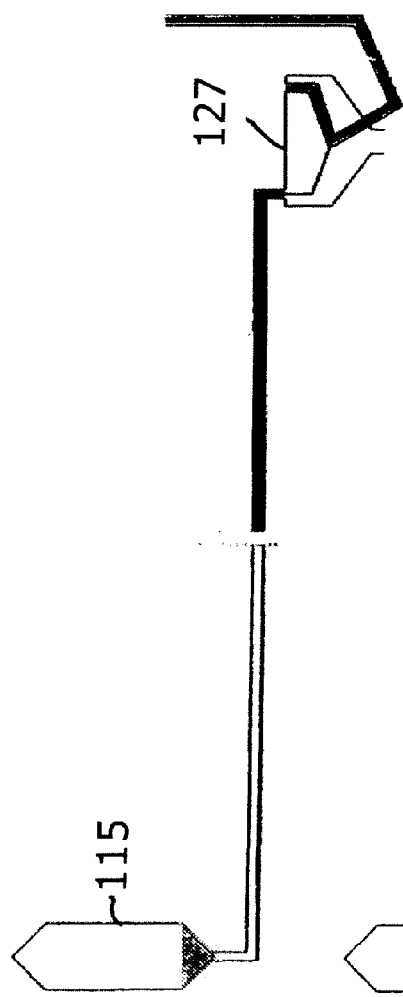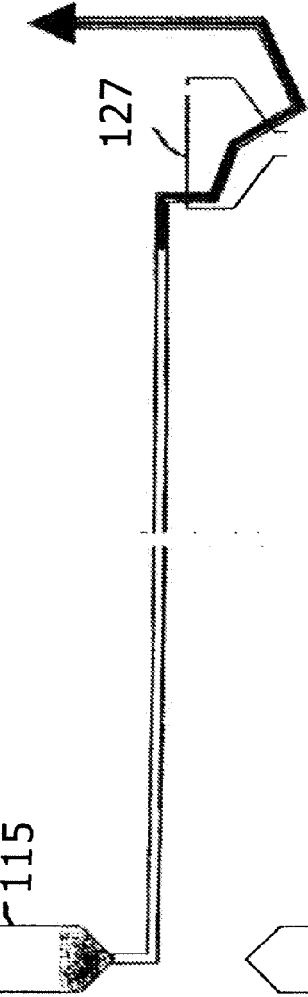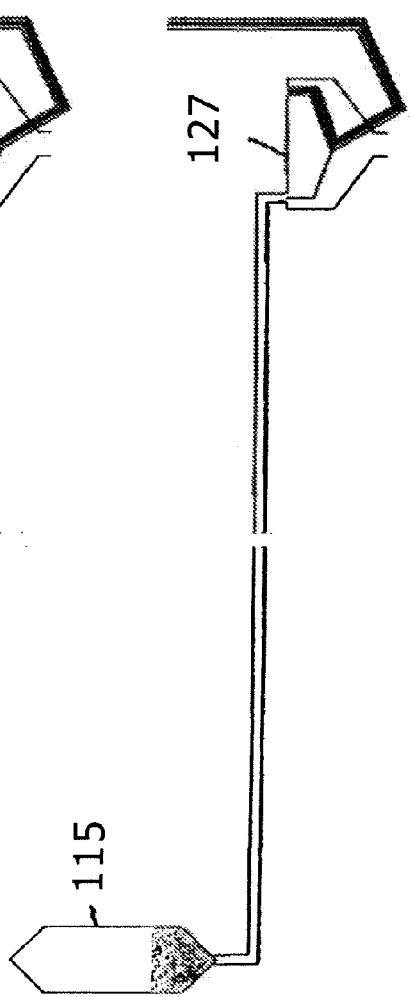

MILK CONVEYER DEVICE

CROSS-REFERENCE TO RELATED APPLICATIONS:

This is a continuation of pending U.S. application Ser. No. 10/739,310, filed Dec. 19, 2003, which claims priority from U.S. Provisional Application Ser. No. 60/434,415, filed Dec. 19, 2002. The contents of both of the above-identified applications are incorporated herein by reference.

FIELD OF THE INVENTION

The invention relates to a milk conveyer device and in particular to a milk conveyer device comprising functionality for analysing a characteristic of the milk.

BACKGROUND OF THE INVENTION

Milk obtained from milking of animals, such as cows or goats, has been a central product of agricultural production for many centuries. In recent decades, the use of automatic milking equipment has become predominant in industrialised countries due to the associated improvement in speed and efficiency.

In addition, it has become common place to analyse the milk from the animals in order to determine the milk quality and health of the animal. Therefore, some methods have been developed to allow for an analysis to be performed as part of an automated milking process. Specifically, analysis equipment has been developed that can chemically analyse milk samples taking from the milk produced by the milking. A chemical analysis may be performed at the site of the milking thereby allowing an individual farmer to test and analyse the milk as part of the milking process.

However, conventional milking systems are cumbersome to use in connection with the analysis equipment. For example, farmers typically have only one analysis element but may have more than one milking unit, each with milking attachment, such as a set of teat cups, for attaching to an animal to be milked. Therefore, performing an analysis typically involves disconnecting the analysis system from one milking unit, cleaning the analysis system, connecting it to another milking unit, generating a milk sample and performing the analysis. This is a very cumbersome operation, which requires significant manual intervention by the farmer. It is very time consuming, increases the workload and reduces the efficiency and productivity of the milking process.

Furthermore, insufficient cleaning results in the analysis samples being polluted thereby resulting in inaccurate or erroneous analysis results. In order to achieve sufficient cleaning, current health and hygiene standards require that the analysis equipment is thoroughly cleaned by flushing the system with significant amounts of water or of a water-based cleaning solution between analyses. Hence, conventional milking analysis systems are required to be flushed with a water-based cleaning solution to remove remnants from a previous analysis.

Systems for extracting milk samples are known from other patents such as the DE 19547892 patent wherein milk samples are extracted automatically. The milk yield being held in a collector vessel under vacuum, mixed with air when milking is over, after which a part of it is fed to a sampling vessel. The milk is delivered from the latter vessel to an analysing unit for immediate analysis. The milk remaining in the collector vessel is only extracted after analysis is complete, and is fed either to a pipe for usable milk, or to one for non-usable milk, dependent on the result. The first jets of milk when milking starts can be extracted via the pipe for non-usable milk. Before storing milk in the sampling vessel, milk can be directed via the latter into the pipe for non-usable milk, until the preceding sample is displaced.

Another example of a device for extracting milk sample is described in patent DE 3502858, which describes a device for drawing off milk samples from a delivery line, the device is used to divert milk into the sample flask by means of clocked pulses. The object of the invention is to achieve, by means of the above mentioned device, a representative, virtually carry-over-free sample even if the delivery rate changes during a sampling operation.

A third example of a system for extracting milk samples is described in patent DE 4343717 A1, which describes a method and apparatus for taking a milk sample representative of a volume of milk. The method and apparatus minimising the risk of contamination of the milk sample by milk originating from another supply. According to the invention a major component flow of milk is branched off from a main flow and directly conducted to a mixing tank. The mixing tank is flushed by a quantity of milk before the milk branched off in a minor component flow from the main flow and conveyed to the mixing tank and collected therein.

Hence, current systems for analysing milk have a number of disadvantages including being cumbersome, wasteful and time consuming. An improved milking arrangement for analysing the milk would be advantageous.

SUMMARY OF THE INVENTION

Accordingly, the invention seeks to provide an improved analysing system for analysing the milk preferably alleviating or mitigating one or more of the disadvantages of the prior art singly or in combination.

According to a first aspect of the invention, there is provided a milk conveyer device for a milking arrangement having a milk storage reservoir; at least one milking unit comprising a milking attachment for attaching to an animal to be milked; a main milk conduit, coupled to the milking attachment and the milk storage reservoir, for conveying milk from the milking attachment to the storage reservoir; the milk conveyer device comprising: an analysis element for analysing at least one selected characteristic of an analysis milk sample generated from a milk analysis quantity; at least one sample unit comprising a sample element for extracting sample milk quantities from the milk of the main milk conduit; a sample reservoir coupled to the sample element for collecting the sample milk quantities to generate the milk analysis quantity; an analysis conduit, coupled to the sample reservoir and operable to be coupled to the analysis element, for conveying the milk analysis quantity from the sample reservoir to the analysis element, wherein at least part of the milk analysis quantity provides a cleaning effect of at least the analysis conduit thereby reducing residues of a previous milk analysis quantity conveyed to the analysis element through the analysis conduit.

It should be understood that, in any aspect of the present invention, a milking unit with a milking attachment may comprise at least one teat cup to be attached to an animal to be milked. For example, the milking unit may be implemented as a part of a so-called Voluntary Milk System which is commercially available from DeLaval International AB. The Voluntary Milk System comprises a milking robot which is ready to receive and milk a cow whenever a cow approaches the milking robot. A device with an optical system automatically cleans every teat of the cow and mounts a set of teat cups to the udder of the cow. Thereby, measurement of the milked quantity of each individual udder part is made possible. The milked quantity of each individual cow is collected before the quantity is being led to the milk storage reservoir. Alternatively, the milked quantity may be disposed if, for example, the cell count is too high, which may be an indication of mastitis. In other embodiments of the invention, the milking unit and milking attachment comprises a conventional system where teat cups are attached to the udder of the cow in a milking parlour.

The inventors of the current invention have realised that contrary to the current belief, a self cleaning milk conveyer device may provide a number of advantages. Hence, in contrast to the current understanding and prescribed standards for milking arrangements, the current invention provides a system wherein the milk being analysed itself provides a cleaning effect. Specifically, the cleaning effect may be applied to the part of the milk conveyer device involved in the analysis process, and in particular the analysis conduit may be cleaned by at least a part of the milk analysis quantity itself. This allows for an analysis process to be applied that does not require separate cleaning fluids to be used between different analysis samples. Furthermore, as a cleaning effect is provided by the milk analysis quantity, a milk conveyer device may be implemented where no separate cleaning step of components of the device is required but rather the cleaning is provided by the milk being conveyed. Hence, the invention allows for a milking system being significantly less time consuming and/or cumbersome and/or wasteful than conventional milking systems. In particular, the invention provides for a system, the operation of which requires less labour work than the operation of conventional systems, and which provides a reduced or even eliminated degree of interruption in a milking/analysis procedure. It should be understood that the self-cleaning process is normally carried out following milking of each individual animal in a batch comprising a plurality of animals, whereas additional cleaning with a water-based cleaning solution is usually carried out upon completion of a milking process, i.e. between two batches.

In a typical embodiment, the cleaning effect is mainly of components associated with the sample reservoir and/or analysis conduit but in other embodiments the cleaning effect extends to other components and aspects of the milk conveyer device, including the analysis element and components associated therewith. In some embodiments, no other cleaning is provided for some of the components, but in other embodiments the cleaning effect of the milk analysis quantity may be complemented by other cleaning steps. The cleaning effect may be achieved by part of the milk analysis quantity flushing out a component of the analysis system prior to the milk analysis sample being taken. Hence, preferably impurities and remnants of previous milk samples are flushed out before a milk analysis sample is taken from the milk analysis quantity.

According to another feature of the invention, the cleaning effect comprises a cleaning effect of at least one of the analysis conduit and the analysis element. Hence, the cleaning effect is preferably associated with analysis part of the milking system, and by using the milk analysis quantity to provide a cleaning effect, the requirement for additional or alternative cleaning by using a cleaning solution can be significantly reduced or eliminated.

According to another feature of the invention, the cleaning effect reduces a concentration of the previous milk analysis quantity in the analysis milk sample to less than 3%, such as less than 1.5%, less than 1% or less than 0.75%. Hence, preferably the milk conveyer device is designed and dimensioned to provide for a substantial cleaning effect. For example, the volume of the milk analysis quantity may be designed such that it causes most of the previous milk analysis quantity to be flushed out before the sample is taken. Designing the system to result in less than 3% of a previous milk analysis quantity to be present in the measurement of the current milk analysis quantity results in an acceptable margin of error. This allows for no other cleaning process of the analysis components to be required thus significantly reducing the time consumption of the analysis process.

According to another feature of the invention, the milk conveyer device comprises no other means for providing cleaning liquids to achieve a cleaning effect. Hence, by designing the system to require no other cleaning liquids than milk to be present, a more hygienic milking system with significantly less risk of contamination is achieved. Specifically, as preferably the only liquid in the system is milk, a leftover or mixing of milk from different milking or analysis processes will have little impact on the analysis quality or analysis accuracy. Specifically, it allows for all liquid in the system to be collected in the same container and thus reduces waste and increases hygiene, as no valve systems are required for water solutions or other external cleaning liquids during a milking process.

According to another feature of the invention, the milk conveyer device is operable to prevent any other liquid than the milk analysis quantities to enter the analysis conduit. The analysis conduit is thus kept free of other liquids than milk thereby reducing the risk of contamination or mixing with other liquids. This improves the accuracy of the analysis process, and allows for the sample milk which is the only liquid in the analysis conduit to be fed directly to the storage reservoir. In preferred embodiments of the invention, the mechanical design of the system is simplified, as there is no need for valve systems for controlling the flow of other liquids but milk.

The flow through the analysis conduit is preferably controlled such that the flow results in a significant cleaning effect. The control of the flow may be dynamically controlled and involve a controller reacting to measurements from sensors. In other embodiments, the control of the flow is simply achieved through the design of the milk conveyer device, for example through the choice of parameters such as the cross area of the analysis conduit or the opening of valves. In most embodiments, the analysis conduit has a length of 1-30 m with an inner diameter of 1-5 mm.

According to another feature of the invention, the analysis element is operable to generate the analysis milk sample by extraction of a milk sample from the milk analysis quantity towards the end of a milk analysis quantity flow. In some embodiments, the initial part of the milk analysis quantity is used to clean elements of the milk conveyer device and specifically the analysis conduit. The analysis milk sample is preferably taken from the latter part of the milk analysis quantity as the cleaning effect has preferably had an effect by then. The less contaminated milk analysis sample ensures an improved analysis.

According to another feature of the invention, the sample reservoir comprises a gas inlet valve operable to open the sample reservoir to a gas thereby causing a pressure to be exerted on the milk analysis quantity in excess of the pressure of the analysis conduit. One suitable and implementation efficient method for controlling the flow of the milk analysis quantity in the analysis conduit is to control the pressure on the milk analysis quantity in the sample reservoir. This may preferably be achieved through controlling a valve coupled to a gas of higher pressure than in the analysis conduit. Preferably, the analysis conduit is at lower than atmospheric level and the gas is simply atmospheric air.

According to another feature of the invention, the milk conveyer device is operable to generate at least one gas bubble in a milk analysis quantity flow through the analysis conduit. The gas bubble, for example an air bubble, is preferably generated inherently by the system as part of the initialisation of the flow of the milk analysis quantity. One option is to let air into the analysis conduit prior to beginning the flow of the milk analysis quantity. Experiments have shown that the presence of air bubbles enhances the cleaning effect of the milk analysis quantity.

According to a second aspect of the invention and/or according to another feature of the invention, there is provided a milk conveyer device for a milking arrangement having a milk storage reservoir; at least one milking unit comprising a milking attachment for attaching to an animal to be milked; a main milk conduit, coupled to the milking attachment and the milk storage reservoir, for conveying milk from the milking attachment to the storage reservoir; the milk conveyer device comprising: an analysis element for analysing at least one selected characteristic of an analysis milk sample generated from a milk analysis quantity; a plurality of sample units, each of which comprises a sample element for extracting sample milk quantities from the milk of the main milk conduit; a sample reservoir coupled to the sample element for collecting the sample milk quantities to generate the milk analysis quantity; an analysis conduit, coupled to the sample reservoir, for conveying the milk analysis quantity from the sample reservoir to the analysis element; and a selector unit coupled to the plurality of analysis conduits of the milk sample units, the selector unit being operable to couple milk from one of the plurality of analysis conduits to the analysis element at a time.

Even though it is indicated above that the milk conveyer preferably comprises both the feature that at least a part of the milk provides a cleaning effect and the selector unit it is to be understood that the present invention also encompasses milk conveyers having only the cleaning feature or the selector unit.

Preferably, the milk conveyer device thus comprises a plurality of milk sample units coupled to a selector unit operable to couple milk from any of the milk sample units to the analysis element. The selector unit may e.g. be an integral part of the analysis element or the analysis element may e.g. comprise two or more completely separate units. Hence, the selector unit and the analysis element may be two completely separate units and may be located at different physical locations. The selector unit may couple all, most, some or only a small proportion of the milk analysis quantity to the analysis element. Further, the analysis element may use only a small fraction of the received milk analysis quantity for the analysis.

The selector unit allows for a plurality of milk sample units to be permanently coupled to the analysis element and the selection of which milk sample unit to analyse samples from can be achieved by a simple control of the selector unit. This significantly facilitates the process of milking and analysing milk from a plurality of animals and thus allows for a much simpler, less cumbersome and time consuming process, as no interruption of the milking process is required.

According to another feature of the invention, the selector unit is a multi-valve unit. This provides for a suitable implementation of a selector unit.

According to another embodiment of the selector unit, it may comprise a plurality of sample stations, each sample station comprises an inlet for the milk to be tested, an outlet for the superfluous milk and an access point, accessible by a collection member for extracting a milk sample. The selector unit may further comprise at least one rinsing station for rinsing of the collection member.

According to another feature of the invention, the selector unit may have access points preferably comprising covers for preventing leakage of air into the system, the cover preferably being constituted by a penetrable plug preferably being made from silicone, rubber or the like, a valve or a moveable slide cover.

According to another feature of the invention, there is provided means for generating a low pressure in a chamber of the selector unit. Preferably a pressure differential is created between the sample reservoir and the chamber of the selector unit. The pressure differential may be created by lowering the pressure of the chamber of the selector unit for example by using a pump or may e.g. be achieved through mounting the selector unit lower than the sample reservoir. The pressure differential biases the milk analysis quantity from the sample reservoir towards the selector unit and thus provides for a suitable way of establishing the flow.

According to another feature of the invention, the milk analysis element further comprises a dosage unit for generating an analysis dosage of the analysis milk sample. Typically, only a very small quantity of milk is required for the analysis and a dosage unit provides the advantage of being able to generate a suitable dose with an acceptable accuracy.

According to another feature of the invention, the selector unit comprises: a chamber, an inlet to a chamber for each of the plurality of analysis conduits for each milk sample unit, each inlet being operable to provide a flow of milk analysis quantities into the chamber, an outlet coupled to the milk analysis element, and a moveable collection member coupled to the outlet of the selector unit, the moveable collection member being operable to move a collection element to the flow of a selected inlet thereby providing a flow connection from the selected inlet to the outlet. This allows for a suitable implementation of a selector unit and specifically allows for a selector unit that can easily be controlled.

According to another feature of the invention, the selector unit of the milk analysis element is operable to collect milk of the milk analysis quantities not being coupled to the milk analysis element, or to guide such milk to the storage reservoir.

The selector unit is coupled to the milk storage reservoir whereby the collected milk is conveyed to the storage reservoir. Hence, advantageously any left over milk not coupled to the analysis element may be fed to the storage reservoir. Consequently, the left over milk is not wasted but is combined with the milk fed directly to the storage reservoir by the main milk conduit. However, it should be understood that, in alternative embodiments of the invention, any left over milk may be disposed.

According to a third aspect of the invention, there is provided a milk conveyer device for a milking arrangement having a milk storage reservoir; at least one milking unit comprising a milking attachment for attaching to an animal to be milked; a main milk conduit, coupled to the milking attachment and the milk storage reservoir, for conveying milk from the milking attachment to the storage reservoir;

the milk conveyer device comprising: an analysis element for analysing at least one selected characteristic of an analysis milk sample generated from a milk analysis quantity; at least one sample unit comprising a sample element for extracting sample milk quantities from the milk of the main milk conduit; a sample reservoir coupled to the sample element for collecting the sample milk quantities to generate the milk analysis quantity; an analysis conduit, coupled to the sample reservoir and operable to be coupled to the analysis element, for conveying the milk analysis quantity from the sample reservoir to the analysis element; and wherein a flow of at least one milk analysis quantity in the analysis conduit has a flow profile comprising a higher flow rate in an earlier time period and a lower flow rate in a later time period.

The flow profile may be created through a dynamic controller measuring the current flow and controlling the flow accordingly. In other embodiments, the flow profile may be achieved through the design of the milk conveyer system. The flow rate within each time interval may be relatively constant or may vary within each time interval. The flow rate may for example refer to the highest flow rate in a time interval, the lowest flow rate in a time interval or to an average flow rate in a time interval. In one embodiment, the flow profile for the milk analysis quantity is a continually decreasing flow rate.

A higher flow rate in an earlier time interval may provide for an increased cleaning effect. Specifically, the milk analysis quantity may more effectively flush out previous impurities and milk remnants at a higher flow rate. However, a lower flow rate facilitates flow control and coupling and sample extraction through the analysis components of the systems. Hence, by having a varying flow rate the flow rate can be optimised for the desired effects at different times.

According to another feature of the invention, the sample reservoir comprises an outlet valve coupled to the analysis conduit.

Hence, advantageously the variation in flow rate may be achieved by control of an outlet valve from the sample reservoir. This provides an accurate and efficient control that can be achieved through simple mechanisms.

According to another feature of the invention, the sample reservoir comprises a quantity sensor for detecting a level of the milk analysis quantity remaining in the sample reservoir, and means for controlling the outlet valve in response to an output of the quantity sensor.

In some embodiments a quantity detector may be used to detect the remaining milk quantity in the sample reservoir. When the quantity falls below a given level, the valve may be adjusted to provide a lower flow rate. This provides for a simple mechanism that can easily be implemented and allows the flow rate to be varied.

According to another feature of the invention, the sample reservoir comprises a gas inlet valve for coupling a gas to the sample reservoir to provide a flow pressure to the milk analysis quantity.

Hence, advantageously the variation in flow rate may be achieved by control of a gas inlet valve from the sample reservoir. This provides an accurate and efficient control that can be achieved through simple mechanisms.

According to another feature of the invention, the sample reservoir comprises a quantity sensor for detecting a level of the milk analysis quantity remaining in the sample reservoir, and means for controlling the gas inlet valve in response to an output of the quantity sensor.

In some embodiments a quantity detector may be used to detect the remaining milk quantity in the sample reservoir. When the quantity falls below a given level, the valve may be adjusted to provide a lower flow rate. This provides for a simple mechanism that can easily be implemented and allows the flow rate to be varied.

According to a different feature of the invention, the milk sample unit is operable to extract sample milk quantities distributed over an extended period of a milking process for a single animal such that the milk analysis quantity comprise contributions from a plurality of sample milk quantities extracted. Specifically, the milk sample unit may be operable to perform proportional sampling of the milk.

Consequently, the milk analysis quantity is preferably generated from milk analysis samples taken over an extended period, which preferably has a duration comparable to the total time of a milking process. Hence, the milk analysis quantity may comprise a representative sample of the milk produced throughout the milking process and thus represent a suitable average of the milk produced. In milking of for example cows, the concentration of e.g. urea varies through the milking process. Hence, a sample taken at a given instant may not be representative as the concentration will depend on when the sample was taken. Therefore, a sampling over an extended period provides for an improved analysis to be performed and improves the diagnostic process based on the analysis. It will thus be understood that the proportional sampling mentioned above may either result in a sample volume which is proportional to the duration of the milking process, or in a sample volume which is proportional to the volume produced by an animal in a milking process. In an embodiment of the invention, the system may be adapted to foresee the volume of a subsequent milking process of an animal, based on volumes of previous milking process of that animal, and to control the proportional sampling accordingly.

According to another feature of the invention, the milk conveyer device comprises an outlet valve between the sample reservoir and the analysis conduit, the outlet valve being operable to be closed during collection of sample milk quantities and opened during conveying of the milk analysis quantity to the analysis element.

The collection and emptying of sampled milk in the sample reservoir may advantageously be at least partly controlled by the gas inlet valve. Specifically, the gas inlet valve may be closed when the milk analysis quantity has been emptied from the sample reservoir and before the milk analysis quantity has been analysed. This allows for the milking attachment to be moved to a different animal, and a new milking process is begun before the milk analysis quantity of the first animal has been analysed.

According to another feature of the invention, the milk conveyer device comprises a conduit inlet gas valve coupled to the analysis conduit towards the outlet valve and operable to open when the outlet valve closes thereby providing a gas exerting a pressure on the milk analysis quantity in the analysis conduit.

Preferably, the flow of the milk analysis quantity in the analysis conduit may be controlled by a gas, controlled by the conduit inlet gas valve. The gas may exert a pressure on the milk analysis quantity in the analysis conduit thereby assisting in producing the flow. Especially, this may allow for the passage to the sample reservoir to be closed without creating a vacuum hampering the flow of the milk analysis quantity in the analysis conduit. Furthermore, the valve may be closed in order to hamper or hinder the flow of the milk analysis quantity in the analysis conduit and can thus be used to retain at least a part of the milk analysis quantity in the analysis conduit. Hence, the conduit inlet gas valve may significantly facilitate and enhance the control of the flow of the milk analysis quantity in the analysis conduit. Preferably the gas is atmospheric air.

According to another feature of the invention, the milk conveyer device comprises a milk flow sensor operable to detect milk flow in the analysis conduit; and a controller for controlling the conduit inlet gas valve to close when the milk flow sensor has detected that a given amount of milk has been supplied through the analysis conduit. Thus, the conduit inlet gas valve is preferably closed when the sample reservoir is empty or nearly empty.

A milk flow sensor may provide the input allowing a controller to control the gas inlet valve to regulate the flow of the milk analysis quantity as desired or required.

According to another feature of the invention, the milk conveyer device further comprising a controller operable to close the conduit inlet gas valve when at least a part of the milk analysis quantity is in the analysis conduit. This may specifically allow for the conduit inlet gas valve to be controlled such that at least some of the milk analysis quantity is retained in the analysis conduit until such time that it is needed by the analysis element. In particular, a part of the milk analysis quantity may thus be stored in the analysis conduit while the analysis element is performing an analysis on another milk analysis quantity. When the analysis element is ready to analyse the milk analysis quantity, this may be extracted from the analysis conduit by any suitable method, for example by pumping it out or opening the gas inlet valve again. The advantage of improved flow control and thus improved processing of a plurality of milk analysis quantities may thus be provided.

According to another feature of the invention, the analysis conduit is at a lower pressure than the sample reservoir during conveying of the milk analysis quantity to the analysis element. This allows for an easy to implement and efficient means of producing a flow from the sample reservoir to the analysis element.

According to another feature of the invention, the sample reservoir comprises a mixer for mixing the milk samples. This allows for an improved mixing of the milk analysis samples thereby ensuring that any sample from the milk analysis quantity used for analysis is representative of the entire sampled quantity.

According to another feature of the invention, the milk conveyer device comprises at least a first sensor for detecting gas bubbles in a flow of milk in the analysis conduit. The detection of gas bubbles or specifically air bubbles may be achieved through use of for example optical detectors or other suitable means. The detection of gas bubbles allows for the control of the flow to be improved as it provides additional information as to whether a milk analysis quantity is currently flowing past the first sensor.

According to another feature of the invention, the milk conveyer device further comprises a processor for determining a beginning of a milk analysis quantity flow from the detection of at least one gas bubble. Alternatively or additionally, the milk conveyer device further comprises a processor for determining an end of a milk analysis quantity flow from the detection of at least one gas bubble. The two functions may be implemented in the same processor and may be based on input from the same sensor. Hence, in an embodiment where the milk analysis quantities in the analysis conduit are interspersed by gas bubbles (e.g. air bubbles), the detection by a sensor of a new gas bubble may be taken as a determination that the end of a milk analysis quantity has passed the sensor. When the sensor changes the indication to indicate that no gas bubble is present at the sensor, this may be taken as an indication that a beginning of a milk analysis quantity has been detected. The detection of beginning and/or ends of a milk analysis quantity provides for a very accurate flow control.

According to another feature of the invention, the milk conveyer device further comprising means for controlling the outlet valve in response to the detection of gas bubbles by the first sensor. This allows for improved flow control and especially allows for very accurate control of the flow of the milk analysis quantity in the analysis conduit. In particular it allows for the outlet valve to be closed when the first sensor detects an end of the milk analysis quantity thus ensuring that the entire milk analysis quantity has exited the sample reservoir.

According to another feature of the invention, the milk conveyer device further comprises a valve controller for controlling the inlet gas valve in response to the detection of gas bubbles by the first sensor. This allows for improved flow control and especially allows for very accurate control of the flow of the milk analysis quantity in the analysis conduit. In particular it allows for the gas inlet valve to be opened when the first sensor detects an end of the milk analysis quantity thus ensuring that the flow of the milk analysis quantity in the analysis conduit is continued when the outlet valve is closed.

According to another feature of the invention, the valve controller is operable to close the gas inlet valve in response to a detection of a gas bubble indicating an end of a milk analysis quantity flow. This allows for improved flow control and especially allows for very accurate control of the flow of the milk analysis quantity in the analysis conduit. In particular, a sensor may be situated along the analysis conduit at a location at which the trailing edge of the milk analysis quantity should stop in order to retain a sufficient amount of the milk analysis quantity in the analysis conduit for later analysis by the analysis element. If this sensor detects a gas bubble indicating the end of a milk analysis quantity, the gas inlet valve may be closed thus creating a vacuum in the analysis conduit preventing further flow. A very accurate system for retaining a desired volume of the milk analysis quantity in the analysis conduit may thus be achieved.

According to a different feature of the invention, the milk analysis quantity is above 200 ml, in order to provide for the self-cleaning effect, and the milk sample quantity is below 100 ml. Generally, the milk sample quantity should be as small as possible in order to have the smallest possible waste. These values have been found to be advantageous and allow for the advantages described to be achieved. In particular, they allow for a suitable cleaning effect to be achieved.

Preferably, the analysis conduit comprises a pipe having an inner cross sectional area of between 1 to 5 $mm^2$ and a length between 1 to 30 m. In a preferred embodiment of the invention, the conduit has an inner cross-sectional area of approximately 4 $mm^2$ upstream of the selector unit, whereas the cross-sectional area of the conduit leading from the selector unit to the analysis element is approximately 1.5 $mm^2$. The analysis conduit is preferably made of low density polyethylene (LD-PE). The pipe may specifically be a hose. These characteristics provide for a suitable analysis conduit that is suitable for most implementations and provide suitable performance and characteristics of the milk conveyer device.

As an example, the at least one selected characteristic comprises a concentration of urea and/or progesterone in the milk analysis sample. With respect to diagnosing mastitis, the selected characteristic comprises an indication of Nagase or LDH content. These parameters are of high importance in determining the milk quality and/or the health of the animal and therefore provide important information to a user of the milk conveyer device.

These and other aspects of the invention will be apparent from and elucidated with reference to the embodiments described hereinafter.

BRIEF DESCRIPTION OF THE DRAWINGS

An embodiment of the invention will be described, by way of example only, with reference to the drawings, in which

FIGS. 5 to 10 are illustrations of elements of a milk conveyer device in accordance with an embodiment of the invention in different phases of operation.

DESCRIPTION OF PREFERRED EMBODIMENTS

Figure 1:
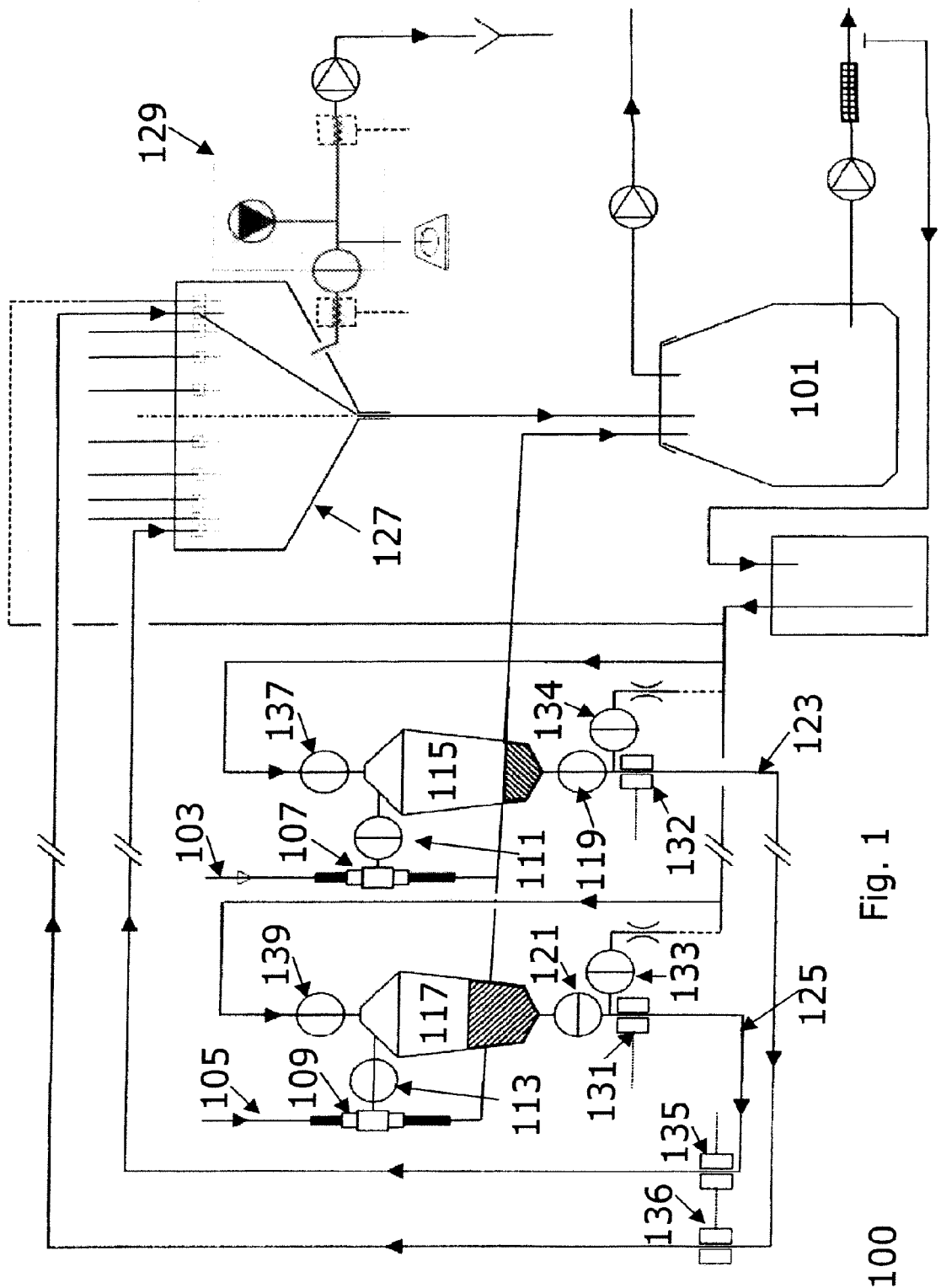
FIG. 1 is an illustration of a milk conveyer device in accordance with a preferred embodiment of the invention.

FIG. 1 is an illustration of a milk conveyer device 100 in accordance with a preferred embodiment of the invention.

The milk conveyer device is to be implemented in a milking arrangement which comprises a milk storage reservoir 101 which collects milk obtained from milking of animals. The milk is obtained from a number of milking points each of which has an associated milking unit (not shown). For clarity and brevity, FIG. 1 illustrates a specific example of two milking points but most implemented milking arrangements will typically have significantly more milking points.

Each milking unit comprises an attachment (not shown) for attaching to an animal to be milked. Such an attachment typically comprises teat cups. The attachment attaches to for example the teats of the udder of a cow, and provides a dynamic suction effect resulting in extraction of milk as is well known in the art. The milking arrangement further comprises a main milk conduit 103, 105 which guides the milk from the attachment to the milk storage reservoir wherein milk from the different milking units are collected.

Figure 2:
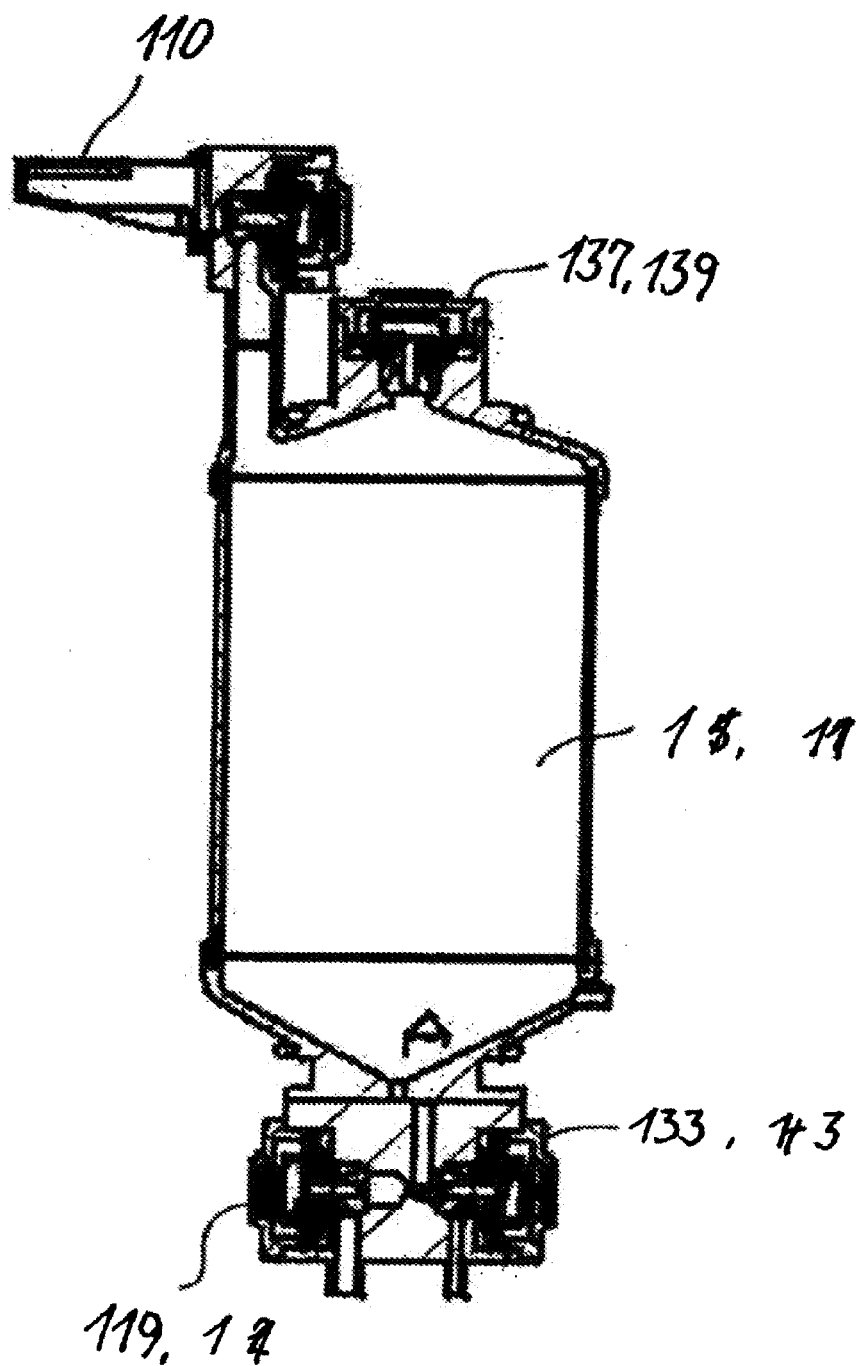
FIG. 2 is an illustration of a sample reservoir with an element for collecting sample milk quantities into the reservoir.

The milk conveyer device further comprises a sample element 107, 109 coupled to the main milk conduit so as to be able to extract sample milk quantities from the flow of milk in the main milk conduit. In the preferred embodiment, the sample element 107, 109 comprises a member 110 (see FIG. 2) with a small aperture extending into a cavity of the main milk conduit 103, 105 allowing for small quantities of milk to enter the aperture whereas the majority of milk bypasses the sample element to continue via the main milk conduit to the milk storage reservoir 101. Preferably the member 110 comprises an arm called knife, comprising at least one slit or aperture for receiving milk. The slit is in contact with the sample reservoir, thus the milk which has been extracted by the slit in the member 110 is preferably transferred to the sample reservoir.

Preferably the member 110 may be controlled in order to extract a representative milk sample from the milk flow in the main milk conduit. Thus during the whole milking session the member 110 extracts milk sample from the main milk conduit. The member may extract 2%, 4%, 6%, 8% or 10% from the milk flow in the main milk conduit. Furthermore the member 110, may be two or more members with different dimensions in order to be able to extract different amount of milk from the main milk conduit. The member 110 is designed for extracting milk from a main milk flow.

The sample elements 107, 109 may further comprise two or more members 110 for extraction of milk samples.

The aperture of the sample element is through a valve 111, 113 coupled to an sample reservoir 115, 117. The valves 111, 113 can open to allow milk to enter the sample, reservoir 115, 117 or close to prevent the milk to enter the sample reservoir. Hence, the valves can be opened to sample milk flowing in the main milk conduit 103, 105 or closed to stop the sampling of milk flowing in the main milk conduit 103, 105.

The milk flowing from the sample element 107, 109 to the storage reservoir 101 flows preferably directly to the storage reservoir 101 (as indicated in FIG. 1 by the lines connecting the storage reservoir 101 with the sample elements 107, 109) but may be buffered in case the result of the analysis of the milk is used as a criteria for allowing milk to flow into the storage reservoir 101. In the latter case, the milk conveyer may comprise a buffer having an outlet comprising a switch valve to guide the milk either to the storage reservoir 101 or to a waste reservoir.

The sample reservoir 115, 117 comprises a collection chamber wherein a plurality of sample milk quantities can be collected. The sample reservoir 115, 117 comprises an outlet valve 119 121 towards the lower end of the collection chamber. The outlet valve 119, 121 is coupled to an analysis conduit 123, 125. When the outlet valve 119, 121 is closed it allows the sample milk quantities to be stored in the collection chamber of the sample reservoir 115, 117, and when the outlet valve is opened, it allows for milk to exit the collection chamber of the sample reservoir 115, 117 to enter the analysis conduit 123, 125.

Figure 11:
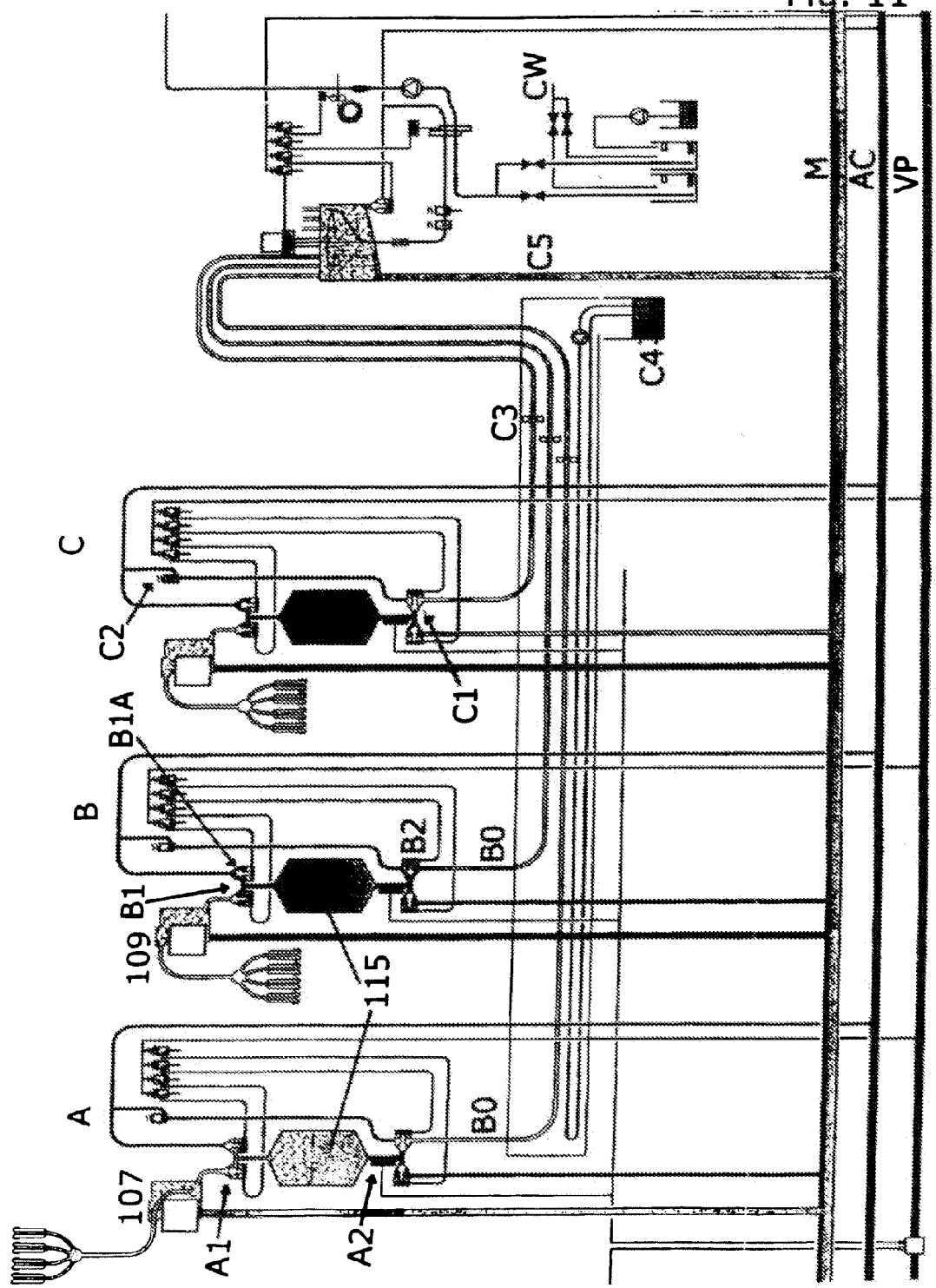
FIG. 11 is a schematic description of a milk conveyer device in accordance with a preferred embodiment of the invention. The figure illustrates the processes for: milk collection, rinsing of the sample hose and dumping of remaining milk

The milk is preferably mixed by a mixer in the vicinity of the bottom of the sample reservoir, preferably by utilising a membrane agitating the milk as described in FIG. 11.

Hence, when a milking process is started the valve 111, 113 is opened to allow sample milk quantities to be extracted from the main milk conduit and enter the collection chamber. The outlet valve 119, 121 is closed to allow the sample milk quantities to be collected in the collection chamber. During a time interval, a milk analysis quantity is collected in the sample reservoir 115, 117 from the sample milk quantities gathered during the milking process. At the end of the time interval, the valve 111, 113 is closed to prevent further milk to enter the collection chamber from the main milk conduit via the sample element 107, 109.

The collection of the sample milk quantities from the main milk conduit 103, 105 may for example be continued for a predetermined time, be manually terminated, be terminated when a suitable milk analysis quantity has been collected or be terminated when milking of an animal is completed which will cause the teat cups to drop off the udder of the cow.

When the collection of the sample milk quantities, which constitute the milk analysis quantity, from the main milk conduit 103, 105 has terminated, the outlet valve 119, 121 is opened. In the preferred embodiment, the pressure of the analysis conduit 123, 125 is lower than that in the collection chamber and consequently the milk analysis quantity will flow from the collection chamber to the analysis conduit 123, 125.

Specifically, the pressure in the analysis conduit 123, 125 is maintained at a lower pressure than atmospheric pressure and the sample reservoir 115, 117 comprises a gas inlet valve 137, 139 which can open to subject the collection chamber to a gas. The gas provides pressure to the milk analysis quantity so as to bias it towards the analysis conduit. In the preferred embodiment, the gas is an atmospheric air and the gas inlet valve simply opens to the surrounding air thereby providing atmospheric pressure. By maintaining the pressure in the analysis conduit 123, 125 below atmospheric level, this will cause the milk analysis quantity to flow into the analysis conduit 123, 125.

In the preferred embodiment, each of the analysis conduits 123, 125 is coupled to a selector unit 127 through which it is possible to transfer milk from the analysis conduit 123, 125 to a milk analysis element 129.

In operation, a computer means which controls the selector unit 127 consequently selects which of the milking points are to be analysed by coupling milk from the corresponding sample element to the analysis element 129. The analysis element 129 performs a chemical analysis, to determine one or more characteristics of at least part of the milk analysis quantity. Specifically, the chemical analysis may determine a concentration of urea or progesterone or any other appropriate characteristic in the milk analysis quantity. It is within the contemplation of the invention, that any suitable analysis may be performed on the milk analysis quantity in order to determine any suitable parameter.

The inventors of the current invention have realised that in a milk conveyer device in accordance with an embodiment of the invention, a cleaning effect can be achieved by the milk analysis quantity in addition to the provision of conveying milk to an analysis element. Specifically, as the initial part of the milk analysis quantity when flowing through the milk conveyer device performs the function of flushing the remnants of previous milk analysis quantities. The analysis milk sample is generated from the latter part of the milk analysis quantity after the first part has cleaned the system.

The milk conveyer device is thus dimensioned such as to allow the milk analysis quantity to provide a significant cleaning effect. Specifically, the flow of the milk analysis quantity through the analysis conduit is dimensioned so as to provide the cleaning effect.

In the preferred embodiment, the analysis conduit comprises a pipe or hose having an inner cross sectional area of approximately 4 $mm^2$ upstream of the selector unit and approximately 1.5 $mm^2$ between the selector unit and the analysis element. The length of the pipe or hose is between 1 and 30 m. For these values, the inventors have realised that for a milk sample quantity above 200 ml and a milk analysis quantity below 100 ml sufficient cleaning of the milking system can be achieved by the milk analysis quantity. Specifically, a carry over of remnants from previous analysis processes can be reduced to less than 3% thereby providing a sufficiently small carry over to allow for a sufficiently accurate analysis to be performed.

Hence, in the preferred embodiment, no other liquid is used for cleaning the milk conveyer device between two consecutive milking processes, i.e. between two consecutive cows except for the milk analysis quantity itself, and the milk conveyer device is constructed so as to prevent that any other liquid enters the analysis conduit and the analysis element. As the only liquid present in the milk carrying parts of the system is milk, all flows can be collected in the storage reservoir without requiring any separation of the milk from other liquids. However, a water-based cleaning solution is used to clean the device following completion of milking of several animals. These animals may constitute a so-called batch.

In the preferred embodiment the control of the valves in the milk conveyer device is furthermore such that at least one gas or specifically air bubble is generated in the milk flow in the analysis conduit. This enhances the cleaning effect provided by the milk analysis quantity.

In the preferred embodiment, the selector unit 127 is a multi-valve unit. Furthermore, as illustrated in FIG. 1, the selector unit 127 is coupled to the storage reservoir 101 such that the milk not being supplied to the analysis element 129 is collected in the storage reservoir 101.

Figure 3:
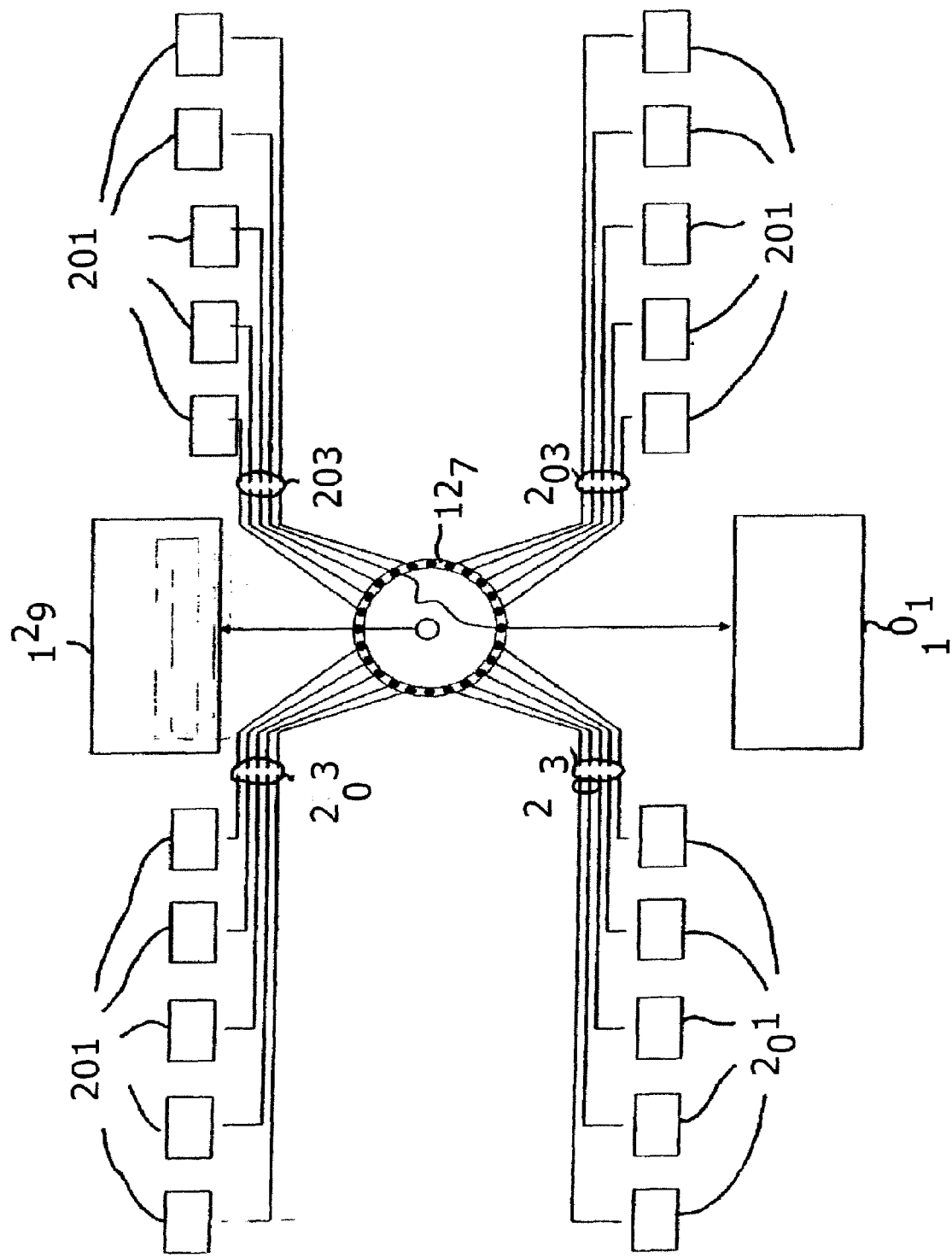
FIG. 3 illustrates the milk conveyer device according to the invention implemented in a milking arrangement with a selector unit in accordance with an embodiment of the invention.

FIG. 3 illustrates the milk conveyer device according to the invention implemented in a milking arrangement with a selector unit 127 in accordance with an embodiment of the invention. The selector unit 127 constitutes a node receiving milk through analysis conduits 203 from a plurality of milking points 201 each having an associated sample unit. Under control of the computer means, the selector unit 127 is connected to the analysis element 129 and the storage reservoir 101. The selector unit selects a single analysis conduit to be coupled to the analysis element 129 for generation of a milk sample to be analysed. Any overflow from this analysis conduit is collected and directed to the storage reservoir.

Figure 4:
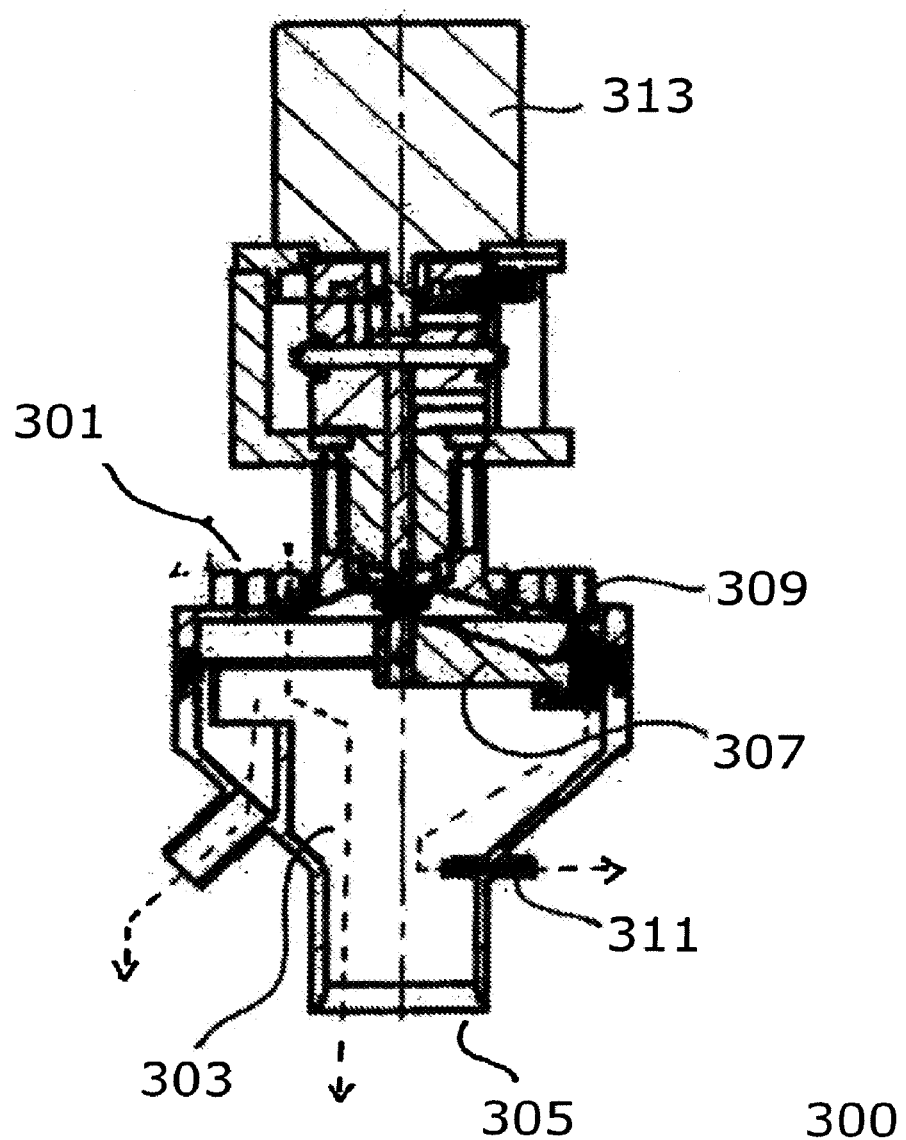
FIG. 4 is an illustration of a multi-valve selector unit in accordance with an embodiment of the invention.

FIG. 4 is an illustration of a multi-valve selector unit 300 in accordance with an embodiment of the invention. The selector unit 300 comprises a plurality of inlets 301 to which the analysis conduits are connected. The selector unit 300 further comprises a chamber 303 into which the milk from the inlets 301 flow. The chamber has an associated outlet 305 through which the overflow milk is collected and fed to the storage reservoir. The selector unit 360 comprises a moveable member or collection element shown in the form of an arm 307. The arm 307 is axially and pivotally mounted such that it is able to rotate a collection member 309 to any of the inlets 301 thereby providing a coupling between the inlet 301 and the collection member 309. The collection member 309 is by the aid of the arm 307 coupled to an outlet 311 through which a part of the analysis quantity is fed to the analysis element. The arm 307 can be rotated by appropriate means, for example by a step motor 313 such that the coupling between one of the inlets 301 and the outlet 311 to the analysis element can be controlled by control of the step motor 313.

In the preferred embodiment, a pressure differential is created between the sample reservoirs and the selector unit to facilitate the flow from the sample reservoirs to the selector unit. In some embodiments this pressure differential may be provided by creating a reduced pressure in the chamber of the selector unit, for example by use of a pump. In other embodiments, a pressure differential is created by gravity, e.g. by the selector unit being mounted lower than the sample reservoirs.

In the preferred embodiment, the analysis element generates a suitable analysis milk sample for the analysis from the milk analysis quantity. Typically, the quantity of the analysis milk sample may be in the order of 30 to 50 ml whereas typically only 0.01 ml of milk is used for the actual analysis.

The operation of the milk conveyer device and in particular the flow of the milk analysis quantities is described in the following with specific reference to FIG. 1 and FIGS. 5 to 10. FIGS. 5 to 10 is an illustration of different components of the milk conveyer device in accordance with an embodiment of the invention in different phases of operation. Specifically, FIGS. 5 to 10 illustrate a sample reservoir 115, an analysis conduit 123 and a selector unit 127.

FIG. 5 illustrates the situation immediately prior to the outlet valve of the sample reservoir being opened. The sample process has been finished and the sample reservoir comprises the milk analysis quantity.

FIG. 6 illustrates the situation after the outlet valve 119 has been opened. Due to the pressure differential between the sample reservoir and the chamber of the selector unit, the milk analysis quantity has started to flow through the analysis conduit.

FIG. 7 illustrates the situation after the entire milk analysis quantity has left the sample reservoir. The initial part of the milk analysis quantity has reached the selector unit and is collected in the chamber and is directed to the storage reservoir. In this situation, no milk is fed to the analysis element. Rather the initial part of the milk analysis quantity is performing a cleaning function cleaning the analysis conduit and removing carry over from the previous milk analysis quantity.

Figure 12:
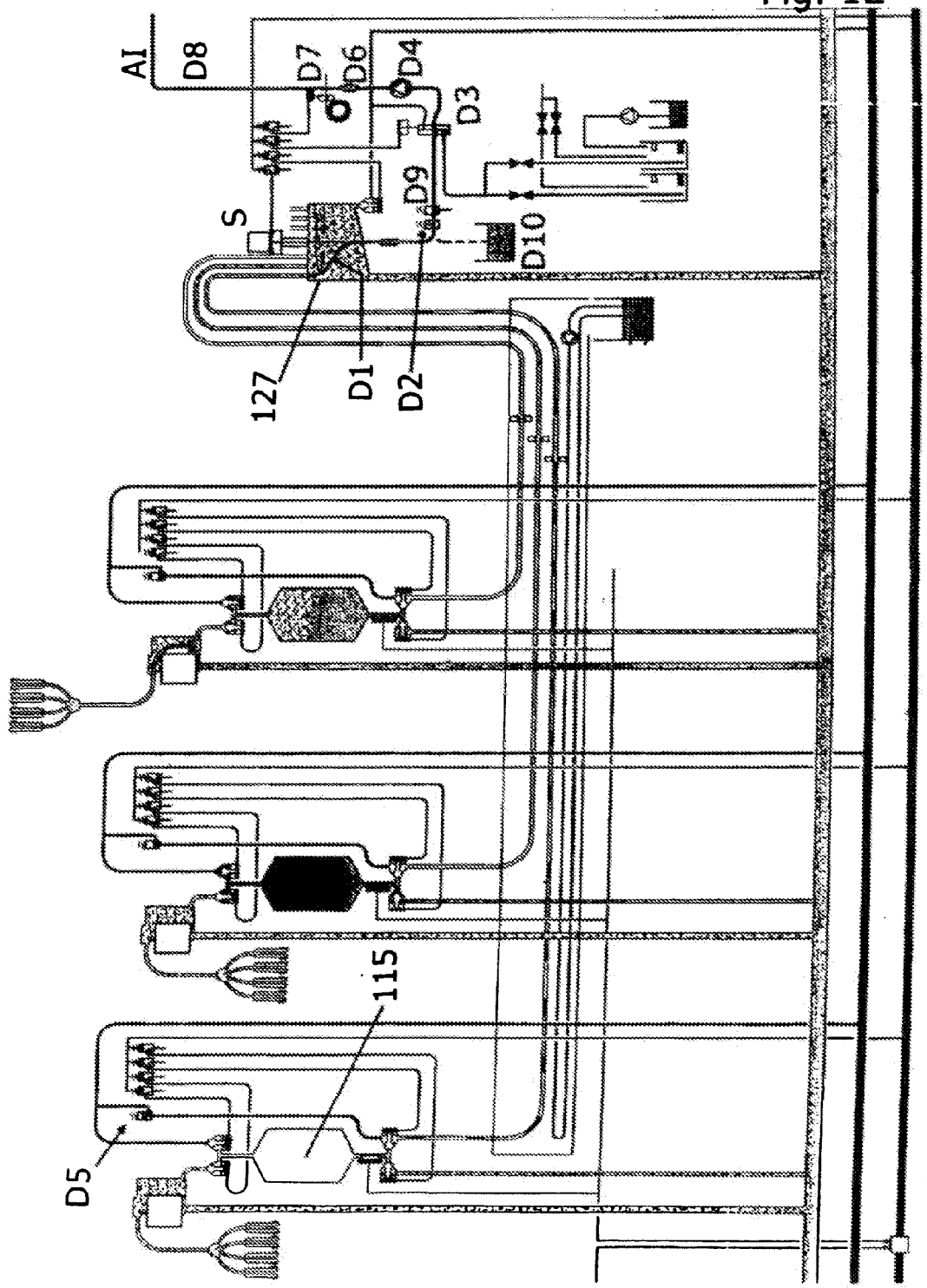
FIG. 12 is a schematic description of the milk conveyer device in figure 11. The figure illustrates the process for transfer of sample to an analysis instrument.
Figure 13:
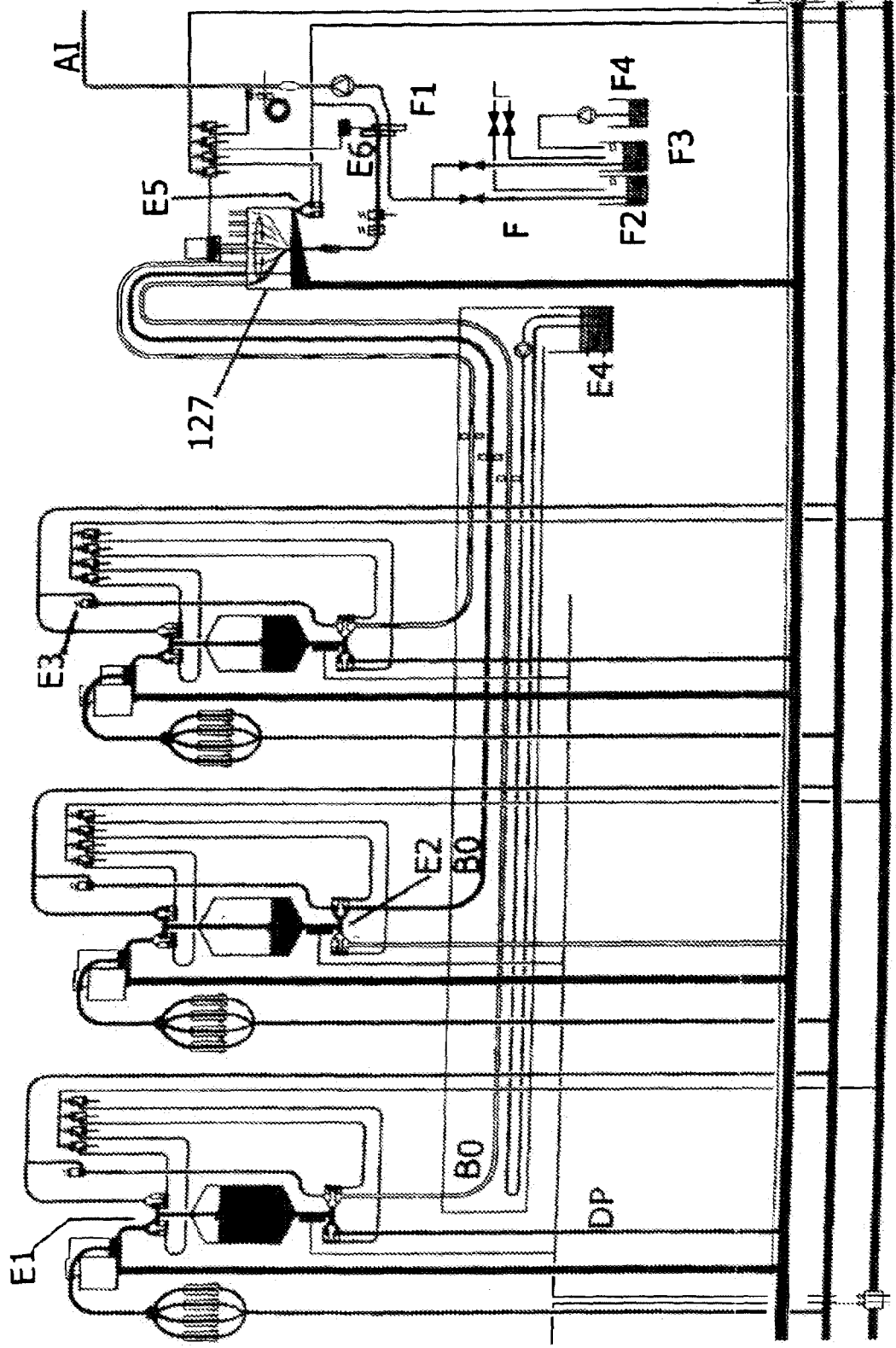
FIG. 13 is a schematic description of the milk conveyer device in FIGS. 11 and 12. The figure illustrates the process of cleaning the device.

In the preferred embodiment, the milk conveyer device further comprises a first sensor 131, 132 (see FIG. 1) close to the outlet valve of the sample reservoir. It is contemplated that the sensor 131, 132 may be left out e.g. as shown in FIG. 11-13. The sensor is operable to detect air bubbles in the flow in the analysis conduit. In addition, the milk conveyer device comprises a conduit inlet gas valve 133, 134 which is coupled to the analysis conduit. The coupling of the inlet gas valve to the analysis conduit is towards the outlet valve of the sample reservoir. When the sensor 131, 132 detects an air bubble indicating that the end of the milk analysis quantity has passed the sensor, the outlet valve of the sample reservoir closes such that the sample reservoir is ready to collect new milk sample quantities. At the same time the conduit inlet gas valve 133, 134 opens to provide a gas exerting a pressure on the milk analysis quantity in the analysis conduit. This causes the flow of the milk analysis quantity to continue in the analysis conduit. In the preferred embodiment, the inlet gas valve simply opens to atmospheric air.

In the preferred embodiment, the milk conveyer device further comprises a second sensor 135, 136, which is located at a distance from the outlet valve further along the analysis conduit 123, 125 towards the selector unit 127. When the second sensor 135, 136 detects an air bubble indicating that the end of the milk analysis quantity has passed the second sensor 135, 136, a control mechanism closes the conduit inlet gas valve 133, 134. Following closing of the inlet gas valve 133, 134, the pressure upstream of the milk analysis quantity, i.e. the pressure behind the milk analysis quantity when seen in the flow direction, will, for a short while, remain higher than the pressure downstream of the milk analysis quantity. Thus, the milk analysis quantity continues while no air is allowed through the inlet gas valve whereby a vacuum develops upstream of the milk analysis quantity. The pressure of the upstream vacuum increases as long as the milk analysis quantity continues to flow. However, when the pressure of the upstream vacuum is equal to the pressure of the vacuum downstream of the milk analysis quantity, i.e. when the pressure differential is equalised, flow of the milk analysis quantity stops. Consequently as shown in FIG. 8 a static situation is obtained wherein a remaining part of the milk analysis quantity is left in the analysis conduit. The remaining part of the milk analysis quantity may remain in the analysis conduit until the selector unit is ready to forward it to the milk analysis element. In a specific embodiment, the second sensor 135, 136 is located such that the analysis conduit extends for approximately three to four meters from the second sensor 135, 136 to the selector unit. For the specific embodiment, this corresponds to approximately 50 ml of the milk analysis quantity remaining in the analysis conduit.

FIG. 9 illustrates the situation after the moveable arm of the selector unit has been moved to the inlet of the analysis conduit. In this situation, the appropriate inlet of the selector unit is coupled to the outlet 311 leading to the analysis element 129. The analysis element comprises a pump, which is operable to pump the remaining part of the milk analysis quantity out of the analysis conduit and into the analysis element 129 as shown in FIG. 9.

The remaining part of the milk analysis quantity, or at least a portion thereof, may be used for the analysis. Said portion of milk is called an analysis milk sample.

As illustrated in FIG. 10, when at least some of the remaining part of the milk analysis quantity has been fed to the analysis element 129, the selector unit 127 may be switched to a different inlet to provide a different analysis quantity to be transferred to the analysis element 129.

It will be clear that a milk conveyer device in accordance with the described embodiment allows for analyses to be performed for a plurality of milking points with very little effort and time consumption. Especially, very little manual control and interaction is required. Further, the milking system provides a self cleaning effect from the milk itself thereby eliminating the requirement for a separate cleaning liquid.

In the preferred embodiment, the flow through the analysis conduit 123, 125 is controlled such that the flow of the milk analysis quantities has a flow profile comprising a higher flow rate in an earlier time period and a lower flow rate in a later time period. Specifically, the initial flow rate is higher than the latter flow rate thereby providing an increased cleaning effect of the initial part of the milk analysis quantity and increased flow control for the latter part of the milk analysis quantity while providing for rapid emptying of the sample reservoirs.

The flow profile is specifically achieved by controlling the opening of one or more of the valves associated with the sample reservoir. In a preferred embodiment, the flow profile is controlled by providing a pulsating open/close signal to the conduit inlet gas valve 133, 134.

Additionally or alternatively, the conduit gas inlet gas valve 133, 134 is operable to be opened wider during the earlier time interval than during the second time interval.

In the preferred embodiments the sample reservoir comprises a quantity sensor for detecting a quantity of the milk analysis quantity remaining in the sample reservoir. A control mechanism is operable to open and close the valves in response to the output of this detector. Specifically, during emptying of the sample reservoir the quantity detector may detect that the remaining milk analysis quantity falls beneath a given threshold, and one or both valves may be closed to some extent thereby limiting the flow of the milk analysis quantity.

In some embodiments different flow rates are achieved by a different gas pressure applied to the milk analysis quantity through the gas inlet valve 137 and the conduit inlet gas valve 133, 134. In this way the flow rate may be reduced when the sample reservoir outlet valve is closed and the conduit inlet gas valve 133, 134 is opened.

In the preferred embodiment, the sample unit is arranged to extract sample milk quantities distributed over an extended period of a milking process. Preferably the sample milk quantities collected into a single milk analysis quantity are extracted regularly from a time towards the beginning of the milking process to a time towards the end of the milking process. Hence, preferably the sample unit performs a proportional sampling of the milk of the main milk conduit.

In the preferred embodiment, the sample reservoir further comprises a mixer for mixing the milk sample quantities. Specifically, the mixer may be a membrane mixer, which is pulsated to provide turbulence in the milk stored in the sample reservoir thereby causing a mixing effect.

FIG. 11 illustrates a preferred embodiment of a milk conveyer device according to the invention wherein the processes of milk collection, rinsing of the sample hose B0 and dumping of the remaining milk is illustrated.

During the milking process the valve A1 between the sample element 107, 109 and the sample reservoir 115 is opened. Approximate 2%, 4%, 6%, 8% or 10% of the yield is conducted from the sample element to the sample reservoir. The milk is gathered during the whole milking process to obtain a representative sample. The equipment preferably manages yields from 7 to 25 kg resulting in sample quantities preferably from 280 to 1000 ml. The A2 membrane close to the outlet of the sample reservoir is agitating the milk entering the sample reservoir in order to provide a proper mixing of the milk. When the milking process is finished, the process of rinsing of the sample hose B0 starts. The valve B1 is closed in order to close the channel to the sample element 109 that also provides vacuum for the sample reservoir. Another valve B1A at the top opens up for air inlet.

The valve B2 at the bottom of the sample reservoir is opened and milk from the sample reservoir rinses the sample hose B0 in order to reduce carry-over from previous samples. To improve the rinsing effect, rinsing milk may be mixed with small amounts of air provided from the speed valve C2.

When the preferred amount of milk sample has been extracted from the sample reservoir 115 the remaining milk from the reservoir may be dumped directly into the main milk pipeline/conduit M after which the milking equipment is ready for the next cow. The milk sample is brought forward in the hose B0 with short intervals of air inlet from the speed valve C2 which in turn is connected to the Air/Cleaning pipeline AC. An air sensor C3 register when the last part of the milk sample passes and shuts of the speed valve C2. Thus the remaining amount of the milk sample is left inside the sample hose until the system is ready to send it to the analysis instrument.

Heating cables may be provided in order to keep the samples in temperature close to 35° C. Shown in the figure is a solution based on circulated hot water C4. However other suitable solutions such as cables etc, for keeping the milk sample warm can also be used. The first part of the sample remaining inside the sample hose is used for rinsing of the sample hose and only the last part of milk is used for analyzing. The first part of the milk, which is used for rinsing the sample hose, may preferably be brought back to the main milk conduit M. The third main pipeline is the vacuum pipeline VP.

FIG. 12 illustrates the embodiment shown in FIG. 11, wherein the process of transferring a milk sample to an analysis instrument is illustrated.

The selector arm D1 inside the selector unit 127 is rotated by a stepper motor S to the desired position and then connected (preferably lifted with vacuum) to that samples port. Further more the shut-off valve D2 is opened and the switch valve D3 is switched from cleaning to analyzing position. The peristaltic pump D4 is activated and the milk sample is pumped towards the analyze instrument AI. Air inlet through the speed valve D5 avoids vacuum in the system. Preferably the sample reservoir 115 is disconnected from air and test hoses which admits milking of another cow to take place. Pressure shocks from the pump D4 are absorbed by a section of flexible hose D6. After that the milk sample passes through a filter D7 in order to remove particles that could damage the function of the analyze instrument. After each sample the filter material is fed forward in order to avoid jamming of the filter. When the last sample has passed the filter a number of feeding operations are performed in order to remove used filter material from the filter feeder. Preferably the filter feeder further comprises means for cutting and collection of used filter material.

The test sample is led forward inside a hose D8 and when the entire sample has passed the shut-off valve D9 (preferably time controlled), is shut off and air is provided from an adjacent electrical operated air inlet valve D10 is a reservoir containing milk samples from cows, which have been treated with antibiotics. The milk in the reservoir D10 is preferably sucked into the system and transferred to the analysis instrument.

The hose between the selector unit 127 and the analysis instrument is preferably cleaned in the same manner as the rest of the system in order to avoid carry-over from the earlier milk sample. Thus the first part of the milk sample entering the hose provides the cleaning effect and the sample which is used in the analysis instrument is extracted from the last part of the milk sample conveyed to the analysis instrument.

FIG. 13 illustrates the embodiment shown in FIG. 11-12, wherein the process of cleaning is illustrated. Cleaning of the milk conveyer device is preferably executed with a portion of cleaning liquid diverted to clean the sample container E1. The cleaning water in the sample reservoir 115 then alternates between E2 passing the dump pipe DP and the milk sample hose B0. The speed valve E3 is opened intermittent to release portions of cleaning water for rinsing the mushroom valve E2. The channel with the sample hoses is warmed up with the heating means E4, such as warm water or the alike, in order to improve the cleaning effect. A mushroom valve E5 located in the bottom part of the selector unit 127 is opened up to clean the selector unit. Cleaning water also flows through the switch valve E6 to clean the selector arm.

The hose D8 connected to the analyze instrument, is cleaned with a small cleaning unit F that can be used separate from the milking conveyer device. With the switch valve E6/F1 in cleaning mode (default mode), hose D8 is connected to the cleaning unit containers F2, F3 and F4.

Detergent F4 is added to heated water in a second container F3 and pumped out for cleaning. Rinsing water is filled up, heated and pumped out through the system. Finally, the hose is rinsed with fresh water. The valve F1 is preferably a secure valve thus if it breaks it returns to a safe mode in order to avoid chemicals to enter the milk conveyer system.

Figure 14:
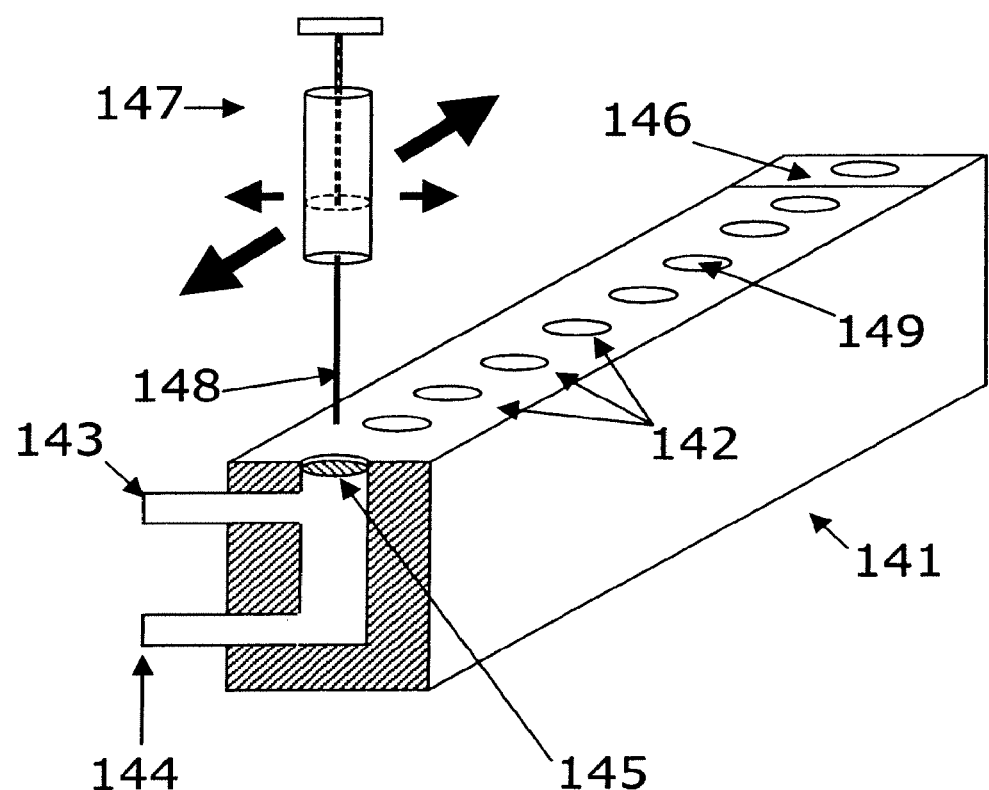
FIG. 14 illustrates another embodiment of a multi-valve selector unit.

FIG. 14 illustrates another embodiment of a multi-valve selector unit 141 in accordance with an embodiment of the invention. The selector unit comprises a block 141 comprising a plurality of sample stations 142. Each sample station comprises an inlet 143 for the milk to be tested, an outlet 144 for the superfluous milk not used in the test and an access point 149, which can be accessed by a collection member 147 such as a needle, pipette or the like for extracting a milk sample. Each access point may be covered with a cover 145 in order to prevent leakage of air into the system. The cover may be penetrated by a part of the collection member 148.

The collection member can be moved across all the sample stations and also to a cleaning station 146 for cleaning of the collection member 147, 148. Furthermore the collection member can be moved to an application station (not shown) for application of a collected milk sample on to a test stick.

Although the present invention has been described in connection with the preferred embodiment, it is not intended to be limited to the specific form set forth herein. Rather, the scope of the present invention is limited only by the accompanying claims.

The invention claimed is:

1. A milk conveyer device for a milking arrangement comprising:
   a milk storage reservoir; at least one milking unit comprising a milking attachment for attaching to an animal to be milked;
   a main milk conduit, coupled to the milking attachment and the milk storage reservoir, for conveying milk from the milking attachment to the storage reservoir
   the milk conveyer device further comprising:
   an analysis element for analysing at least one selected characteristic of an analysis milk sample generated from a milk analysis quantity;
   a plurality of milk sample units, each of which comprises a sample element for extracting sample milk quantities from the milk of the main milk conduit;
   a plurality of sample reservoirs coupled to each of the sample elements for collecting the sample milk quantities to generate the milk analysis quantity;
   a plurality of analysis conduits, coupled to each of the sample reservoirs for conveying the milk analysis quantity from the sample reservoirs to the analysis element; and
   a selector unit coupled to the plurality of analysis conduits of the milk sample units, the selector unit being operable to couple milk from one of the plurality of analysis conduits to the analysis element at a time.

2. A milk conveyor device according to claim 1, wherein the selector unit is an integral part of the analysis element.

3. A milk conveyor device according to claim 1, wherein the analysis element and the selector unit comprise two or more completely separate units.

4. A milk conveyor device according to claim 1, wherein the selector unit is a multi-valve unit.

5. A milk conveyor device according to claim 1, wherein the selector unit comprises a plurality of sample stations, each sample station comprises an inlet for the milk to be tested, an outlet for superfluous milk and an access point, accessible by a collection member for extracting a milk sample.

6. A milk conveyor device according to claim 5, wherein the selector unit further comprises at least one rinsing station for rinsing of the collection member.

7. A milk conveyor device according to claim 1, wherein the selector unit comprises access points comprising covers for preventing leakage of air into the system.

8. A milk conveyor device according to claim 7, wherein the covers being constituted by a penetrable plug, a valve or a moveable slide cover.

9. A milk conveyor device according to claim 8, wherein the penetrable plug is made from silicone or rubber.

10. A milk conveyor device according to claim 1, further comprising means for generating a low pressure in a chamber of the selector unit.

11. A milk conveyor device according to claim 10, wherein the means for generating a low pressure comprises a pump.

12. A milk conveyor device according to claim 10, wherein the means for generating a low pressure comprises mounting the selector unit lower than the sample reservoir.

13. A milk conveyor device according to claim 1, wherein the analysis element further comprises a dosage unit for generating an analysis dosage of the analysis milk sample.

14. A milk conveyor device according to claim 1, wherein the selector unit comprises: a chamber, an inlet to a chamber for each of the plurality of analysis conduits for each milk sample unit, each inlet being operable to provide a flow of milk analysis quantities into the chamber, an outlet coupled to the analysis element, and a moveable collection member coupled to the outlet of the selector unit, the moveable collection member being operable to move a collection element to the flow of a selected inlet thereby providing a flow connection from the selected inlet to the outlet.

15. A milk conveyor device according to claim 1, wherein the selector unit is operable to collect milk of those milk analysis quantities which are not being coupled to the analysis element, or to guide such milk to the storage reservoir.

16. A milk conveyor device according to claim 1, wherein the selector unit is coupled to the milk storage reservoir whereby the collected milk is conveyed to the storage reservoir.

* * * * *